United States Patent
Chang et al.

(10) Patent No.: US 6,664,046 B1
(45) Date of Patent: Dec. 16, 2003

(54) QUANTITATION OF HTERT MRNA EXPRESSION

(75) Inventors: Sheng-Yung Pai Chang, San Francisco, CA (US); Christopher David Santini, Oakland, CA (US)

(73) Assignee: Roche Molecular Systems, Inc., Alameda, CA (US)

( * ) Notice: Subject to any disclaimer, the term of this patent is extended or adjusted under 35 U.S.C. 154(b) by 0 days.

(21) Appl. No.: 09/465,491

(22) Filed: Dec. 16, 1999

(51) Int. Cl.$^7$ ............................ C12Q 1/68; C07H 21/04
(52) U.S. Cl. .................... 435/6; 435/91.1; 435/91.2; 536/23.1; 536/24.3; 536/24.33
(58) Field of Search ...................... 435/6, 91.1, 91.2; 536/23.1, 24.3, 24.33

(56) References Cited

U.S. PATENT DOCUMENTS

| | | | | |
|---|---|---|---|---|
| 5,475,110 A | * | 12/1995 | Hudkins et al. | ............ 546/256 |
| 5,583,016 A | | 12/1996 | Villeponteau et al. | ..... 435/91.3 |
| 5,593,862 A | * | 1/1997 | Hall et al. | ................. 435/69.1 |
| 5,629,154 A | | 5/1997 | Kim et al. | ..................... 435/6 |
| 6,166,178 A | * | 12/2000 | Cech et al. | ................. 530/324 |

FOREIGN PATENT DOCUMENTS

| WO | WO 97/15687 | 5/1997 |
|---|---|---|
| WO | WO 99/01560 | 1/1999 |
| WO | WO 99/40221 | 8/1999 |

OTHER PUBLICATIONS

Kilian et al "Isolation of a candidate human telomerase catalytic subunit gene, which reveals complex splicing pattern in different cell types" Human Molecular Genetics, VOl 6, No. 12, p. 2011–2019, 1997.*

Ulaner et al "Telomerase activity in human development is regulated by human telomerase reverst transcriptase (hTERT) transcription and by altered splicing of hTERT transcripts" Cancer Research, Vol 58, p. 4168–4172, Sep. 1998.*

Strategene Catalog, 1988, p. 39.*

Nankamura et al "Quantitative Reevaluation of telomerase activity in cancerous and noncancerous gastrointestinal tissues" Molecular Carcinogenesis, Vol 26, p. 312–320, Dec. 1999.*

Aogi et al "Comparison of telomerase and CD44 expression as diagnostic tumor markers in lesions of the thyroid" Clinical Cnacer Research, Vol 5, p. 2790–2797, Oct. 1999.*

Wu et al "Correlation of the expression of human telomerase subunits with telomerase activity in normal skin and skin tumors" Cancer, Vol 86, No. 10, p. 2038–2044, Nov. 1999.*

Gelmini et al., 1998, "Rapid, quantitative nonisotopic assay for telomerase activity in human tumors", Clinical Chemistry 44(10):2133–2138.

Hisatomi et al., 1999, "Levels of telomerase catalytic subunit mRNA as a predictor of potential malignancy", International Journal of Oncology 14: 727–732.

Chang, 1999, "Quantitation of Telomerase Activity using Kinetic Telomeric Repeat Amplification Protocol", in PCR Applications (Innis et al., eds.) Chapter 17, Academic Press, San Diego.

Kim et al., Dec. 23, 1994, "Specific Association of Human Telomerase Activity with Immortal Cells and Cancer", Science 266:2011–2015.

Nakamura et al., Aug. 15, 1997, "Telomerase Catalytic Subunit Homologs from Fission Yeast and Human", Science 277:955–959.

Meyerson et al., Aug. 22, 1997, "hEST2, the Putative Human Telomerase Catalytic Subunit Gene, Is Up–Regulated in Tumor Cells and during Immortalization", Cell 90:785–795.

Cong et al., 1999, "The human telomerase catalytic subunit hTERT: organization of the gene and characterization of the promoter", Human Molecular Genetics 8(1):137–142.

Wick et al., 1999, "Genomic organization and promoter characterization of the gene encoding human telomerase reverse transcriptase (hTERT)", Gene 232:97–106.

Pre–publication Draft of Harley and Kim, 1996, "Telomerase and Cancer", in Important Advances in Oncology: 57–67, a supplement to Cancer: Principles and Practice of Oncology (DeVita et al., eds.).

Kilian et al., "Isolation Of A Candidate Human Telomerase Catalytic Subunit Gene, Which Reveals Complex Splicing Patterns In Different Cell Types," Human Molecular Genetics, 1997, vol. 6, No. 12, pp 2011–2019.

Ulaner et al., "Telomerase Activity In Human Development Is Regulated By Human Telomerase Reverse Transcriptase (hTERT) Transcription And By Alternate Splicing Of hTERT Transcripts," Cancer Research, Sep. 1998, vol. 58, pp 4168–4172.

Copy of International Search Report From EP 00 12 7228.

* cited by examiner

Primary Examiner—Gary Benzion
Assistant Examiner—Jeanine Goldberg
(74) Attorney, Agent, or Firm—Pennie & Edmonds LLP

(57) ABSTRACT

Methods and reagents for quantitating the expression of mRNA which encodes an active hTERT protein, which is useful for the diagnosis and the prognosis of cancer.

11 Claims, 4 Drawing Sheets

SEQUENCE LISTING

<160> NUMBER OF SEQ ID NOS: 10

<210> SEQ ID NO 1
<211> LENGTH: 4015
<212> TYPE: DNA
<213> ORGANISM: Homo sapiens

<400> SEQUENCE: 1

```
gcagcgctgc gtcctgctgc gcacgtggga agccctggcc ccggccaccc ccgcgatgcc      60
gcgcgctccc cgctgccgag ccgtgcgctc cctgctgcgc agccactacc gcgaggtgct     120
gccgctggcc acgttcgtgc ggcgcctggg gccccagggc tggcggctgg tgcagcgcgg     180
ggacccggcg gctttccgcg cgctggtggc ccagtgcctg gtgtgcgtgc cctgggacgc     240
acggccgccc cccgccgccc cctccttccg ccaggtgtcc tgcctgaagg agctggtggc     300
ccgagtgctg cagaggctgt gcgagcgcgg cgcgaagaac gtgctggcct tcggcttcgc     360
gctgctggac ggggcccgcg ggggccccc cgaggccttc accaccagcg tgcgcagcta     420
cctgcccaac acggtgaccg acgcactgcg ggggagcggg gcgtggggc tgctgctgcg     480 ccgcgtgggc gacgacgtgc tggttcacct gctggcacgc tgcgcgctct ttgtgctggt     540
ggctcccagc tgcgcctacc aggtgtgcgg gccgccgctg taccagctcg gcgctgccac     600
tcaggcccgg cccccgccac acgctagtgg accccgaagg cgtctgggat gcgaacgggc     660
ctggaaccat agcgtcaggg aggccggggt cccctggc ctgccagccc cgggtgcgag      720
gaggcgcggg ggcagtgcca gccgaagtct gccgttgccc aagaggccca ggcgtggcgc     780
tgcccctgag ccggagcgga cgcccgttgg gcagggtcc tgggcccacc cgggcaggac      840
gcgtggaccg agtgaccgtg gtttctgtgt ggtgtcacct gccagacccg ccgaagaagc     900
cacctctttg gagggtgcgc tctctggcac gcgccactcc cacccatccg tgggccgcca     960
gcaccacgcg ggcccccat ccacatcgcg gccaccacgt ccctgggaca cgccttgtcc     1020
```

-continued

```
cccggtgtac gccgagacca agcacttcct ctactcctca ggcgacaagg agcagctgcg      1080
gccctccttc ctactcagct ctctgaggcc cagcctgact ggcgctcgga ggctcgtgga      1140
gaccatcttt ctgggttcca ggccctggat gccaggcact cccgcaggt tgccccgcct       1200
gccccagcgc tactggcaaa tgcggcccct gtttctggag ctgcttggga accacgcgca      1260
gtgccctac ggggtgctcc tcaagacgca ctgcccgctg cgagctgcgg tcaccccagc       1320
agccggtgtc tgtgcccggg agaagcccca gggctctgtg gcggccccg aggaggagga       1380
cacagacccc cgtcgcctgg tgcagctgct ccgccagcac agcagcccct ggcaggtgta      1440
cggcttcgtg cgggcctgcc tgcgccggct ggtgccccca ggcctctggg gctccaggca      1500
caacgaacgc cgcttcctca ggaacaccaa gaagttcatc tccctgggga agcatgccaa      1560
gctctcgctg caggagctga cgtggaagat gagcgtgcgg gactgcgctt ggctgcgcag      1620
gagcccaggg gttggctgtg ttccggccgc agagcaccgt ctgcgtgagg agatcctggc      1680
caagttcctg cactggctga tgagtgtgta cgtcgtcgag ctgctcaggt ctttctttta      1740
tgtcacggag accacgtttc aaaagaacag gctcttttc taccggaaga gtgtctggag       1800
caagttgcaa agcattggaa tcagacagca cttgaagagg gtgcagctgc gggagctgtc      1860
ggaagcagag gtcaggcagc atcgggaagc caggcccgcc ctgctgacgt ccagactccg      1920
cttcatcccc aagcctgacg ggctgcgcc gattgtgaac atggactacg tcgtgggagc       1980
cagaacgttc cgcagagaaa agagggccga gcgtctcacc tcgagggtga aggcactgtt      2040
cagcgtgctc aactacgagc gggcgcggcg ccccggcctc ctgggcgcct ctgtgctggg      2100
cctggacgat atccacaggg cctggcgcac cttcgtgctg cgtgtgcggg cccaggaccc      2160
gccgcctgag ctgtactttg tcaaggtgga tgtgacgggc gcgtacgaca ccatccccca      2220
ggacaggctc acggaggtca tcgccagcat catcaaaccc cagaacacgt actgcgtgcg      2280
tcggtatgcc gtggtccaga aggccgccca tgggcacgtc cgcaaggcct tcaagagcca      2340
cgtctctacc ttgacagacc tccagccgta catgcgacag ttcgtggctc acctgcagga      2400
gaccagcccg ctgagggatg ccgtcgtcat cgagcagagc tcctccctga atgaggccag      2460
cagtggcctc ttcgacgtct tcctacgctt catgtgccac cacgccgtgc gcatcagggg      2520
caagtcctac gtccagtgcc aggggatccc gcagggctcc atcctctcca cgctgctctg      2580
cagcctgtgc tacggcgaca tggagaacaa gctgtttgcg gggattcggc gggacgggct      2640
gctcctgcgt ttggtggatg atttcttgtt ggtgacacct cacctcaccc acgcgaaaac      2700
cttcctcagg accctggtcc gaggtgtccc tgagtatggc tgcgtggtga acttgcggaa      2760
gacagtggtg aacttccctg tagaagacga ggccctgggt ggcacggctt ttgttcagat      2820
gccggcccac ggcctattcc cctggtgcgg cctgctgctg ataccccgga ccctggaggt      2880
gcagagcgac tactccagct atgcccggac ctccatcaga gccagtctca ccttcaaccg      2940
cggcttcaag gctgggagga acatgcgtcg caaactcttt ggggtcttgc ggctgaagtg      3000
tcacagcctg tttctggatt tgcaggtgaa cagcctccag acgtgtgca ccaacatcta       3060
caagatcctc ctgctgcagg cgtacaggtt tcacgcatgt gtgctgcagc tcccatttca      3120
tcagcaagtt tggaagaacc ccacattttt cctgcgcgtc atctctgaca cggcctccct      3180
ctgctactcc atcctgaaag ccaagaacgc agggatgtcg ctgggggcca gggcgccgc       3240
cggccctctg ccctccgagg ccgtgcagtg gctgtgccac caagcattcc tgctcaagct      3300
gactcgacac cgtgtcacct acgtgccact cctgggtca ctcaggacag cccagacgca       3360
gctgagtcgg aagctcccgg ggacgacgct gactgccctg aggccgcag ccaacccggc       3420
```

```
actgccctca gacttcaaga ccatcctgga ctgatggcca cccgcccaca gccaggccga    3480
gagcagacac cagcagccct gtcacgccgg gctctacgtc ccagggaggg aggggcggcc    3540
cacacccagg cccgcaccgc tgggagtctg aggcctgagt gagtgtttgg ccgaggcctg    3600
catgtccggc tgaaggctga gtgtccggct gaggcctgag cgagtgtcca gccaagggct    3660
gagtgtccag cacacctgcc gtcttcactt ccccacaggc tggcgctcgg ctccacccca    3720
gggccagctt ttcctcacca ggagcccggc ttccactccc cacataggaa tagtccatcc    3780
ccagattcgc cattgttcac ccctcgccct gccctccttt gccttccacc cccaccatcc    3840
aggtggagac cctgagaagg accctgggag ctctgggaat ttggagtgac caaaggtgtg    3900
ccctgtacac aggcgaggac cctgcacctg gatggggtc cctgtgggtc aaattggggg     3960
gaggtgctgt gggagtaaaa tactgaatat atgagttttt cagttttgaa aaaaa         4015
```

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 2

```
catgggcacg tccgcaa                                                     17
```

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 3

```
cgccgaatcc ccgcaaa                                                     17
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4

```
ggcgtggtgg cacatgaa                                                    18
```

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 5

```
tgggcacgtc cgcaa                                                       15
```

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 6

-continued

```
tcatcgagca gagctcctcc ctgaatgagg                                              30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 7
cagcagtggc ctcttcgacg tcttcctacg                                              30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 8
tctaccttga cagacctcca gccgtacatg                                              30

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 9
caatgccagt ggaacca                                                            17

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
ccataccggg tttgagaaca                                                         20
```

QUANTITATION OF HTERT MRNA EXPRESSION

BACKGROUND OF THE INVENTION

1. Field of the Invention

The present invention relates to the field of molecular biology and nucleic acid chemistry. More specifically, it relates to methods and reagents for quantitating expression of mRNA that encodes an active form of hTERT, the catalytic subunit of telomerase, as an indicator of the presence of cancerous cells.

2. Description of Related Art

Telomerase is an RNA-dependent DNA polymerase that synthesizes telomeric DNA. The core enzyme consists of an RNA component that serves as a template for the synthesis of telomeric repeats, and a catalytic subunit with reverse transcriptase activity, designated hTERT (also referred to as hTCS1, hTRT, and hEST2).

Assays of telomerase activity are described in, for example, International Patent Publication No. WO 97/15687, incorporated herein by reference. A PCR-based telomeric repeat amplification protocol (TRAP) is described in Chang, 1999, in PCR Applications (Innis et al., eds.) Chapter 17, Academic Press, San Diego; Kim et al. 1994, Science 266:2011–2015; and U.S. Pat. No. 5,629,154, each incorporated herein by reference. Telomerase activity is not detected in most human somatic cells, but is detected in immortalized cell lines and in human tumors. The detection of elevated telomerase activity in a tissue sample can be used to identify cancerous tissues.

Nakamura et al., 1997, Science 277:955–959, identified the gene encoding the catalytic subunit of human telomerase (designated therein hTRT). They reported that hTRT mRNA was not expressed in telomerase-negative cell lines, but was expressed in telomerase-positive immortal cell lines, and concluded that the expression of mRNA from the human gene correlates with telomerase activity.

Meyerson et al., 1997, Cell 90:785–795, described the cloning of the gene encoding the catalytic subunit of telomerase (designated therein hEST2) and report that it is expressed at high levels in primary tumors, cancer cell lines, and telomerase-positive tissues, but is undetectable in telomerase-negative cell lines and differentiated telomerase-negative tissues. They report that, although they found a general correlation between hEST2 mRNA levels and telomerase activity, these two measures where not present in a constant, predictable ratio. Consequently, Meyerson et al. speculated that other mechanisms besides the modulation of mRNA levels may be important in the regulation of telomerase activity.

Kilian et al., 1997, Human Molecular Genetics 6(12):2011–2019, identified the gene encoding the catalytic subunit of human telomerase (designated therein hTCS 1). They reported that, although the gene is present in a single copy, it is expressed in a complex splicing pattern that gives rise to a number of potential proteins. A number of different transcript sequence variants were identified. By comparing the splice variants with a reference sequence essentially identical to that reported by Nakamura et al., supra, they identified two splice variant deletions, a 36 nucleotide deletion designated α and a 182 nucleotide deletion designated β, as well as 3 different insertions. Deletion of the α region was reported as resulting in a small in-frame 12 amino acid deletion. The β region deletion was reported to encode a truncated protein.

SUMMARY OF INVENTION

The present invention provides reagents, methods, and kits for the quantitation of expression of hTERT mRNA that encodes an active hTERT protein. The reagents, methods, and kits provide and improvement over methods previously described by enabling a more accurate estimate of telomerase activity.

The level of hTERT mRNA expression provides information that assists in the diagnosis of cancers. Telomerase activity, repressed in most normal somatic cells, is reactivated in immortal tumor cells. We have confirmed that telomerase activity is regulated at the level of gene expression, and that the level of hTERT mRNA expression provides a measure of telomerase activity. The present invention provides an accurate and reproducible measure of telomerase activity by selectively measuring mRNA that encodes an active hTERT protein.

The hTERT gene consists of 16 exons and 15 introns spanning about 35 kilobases and encodes 1132 amino acids. Several splice variants have been reported. We have determined that mRNA splice variants which encode an active hTERT protein can be discriminated from the predominant splice variants which encode inactive forms of the hTERT protein based on the presence the β region, the 182 nucleotide deletion encompassing exon 7 and exon 8. The methods of the present invention selectively measure only hTERT mRNA containing the β region and, thus, enable quantitation of essentially only mRNA encoding an active hTERT protein.

One aspect of the invention is the discovery of a previously unobserved splice variant in which there is a deletion of a subregion of the β region which, most likely, corresponds to a deletion of exon 8, specifically. The occurrence of this splice variant represent a previously unrecognized problem in estimating telomerase activity based on hTERT mRNA expression. The present invention provides a solution to this previously unrecognized problem.

One aspect of the invention relates to methods and reagents for quantitating hTERT mRNA in a human sample. The methods and reagents selectively measure primarily mRNA encoding the active form of the hTERT protein, which provides a more accurate surrogate measure of telomerase activity and, thereby provides an improved marker for use in cancer diagnosis.

The methods of the invention involve amplifying a target hTERT mRNA sequence using a pair of primers in which one primer hybridizes to a sequence within exon 8, which is a subregion of the β region, and the other primer hybridizes to a sequence outside the β region, preferably within exon 6, upstream of the β region, and quantitatively detecting the formation of amplification products. Such a primer pair has the property that the amplified mRNA corresponds to primarily mRNA that encodes an active hTERT protein. Particularly preferred amplification primers are described below. The preferred primers are particularly advantageous in that they provide for the specific and efficient amplification of the mRNA sequence.

The detection of amplification can be carried out using a variety of methods, as described below. In a preferred embodiment, the amplified hTERT mRNA sequence is detected by probe hybridization. In a particularly preferred embodiment, the amplified product is detected using a probe which hybridizes to an mRNA sequence at least partially within exon 7, more preferably encompassing the exon7/exon 8 splice junction. Such a probe has the property that it would enable the detection of a splice variant in which only exon 7 is deleted, which has yet to be observed. An exon 7 deletion splice variant would be identified by successful amplification of a product not that did not hybridize to the probe.

Another aspect of the invention relates to methods and reagents for determining the telomerase activity in a human sample, which involves quantitating hTERT mRNA using the methods and reagents of the present invention. The quantity of hTERT mRNA, when calibrated as described herein, provides an estimate of the telomerase activity. The present invention, by measuring essentially only hTERT mRNA which encodes an active hTERT protein, provides a more accurate estimate of telomerase activity.

Another aspect of the invention relates to methods of identifying the presence of cancerous cells in a tissue sample which involves detecting an increased level of hTERT mRNA that encodes an active form of the hTERT protein or, equivalently, an increased level of telomerase activity, using the methods and reagents of the present invention.

Another aspect of the invention relates to oligonucleotides useful as amplification primers or detection probes in the methods of the present invention.

Another aspect of the invention relates to kits useful for quantitating hTERT mRNA comprising one or more of the reagents of the present invention. These kits take a variety of forms. In one embodiment, the kits of the inventions comprise primers and, optionally, probes, as described above. The kits can also comprise one or more amplification reagents, e.g., primers, polymerase, buffers, and nucleoside triphosphates.

DETAILED DESCRIPTION OF THE INVENTION

Figure 1:
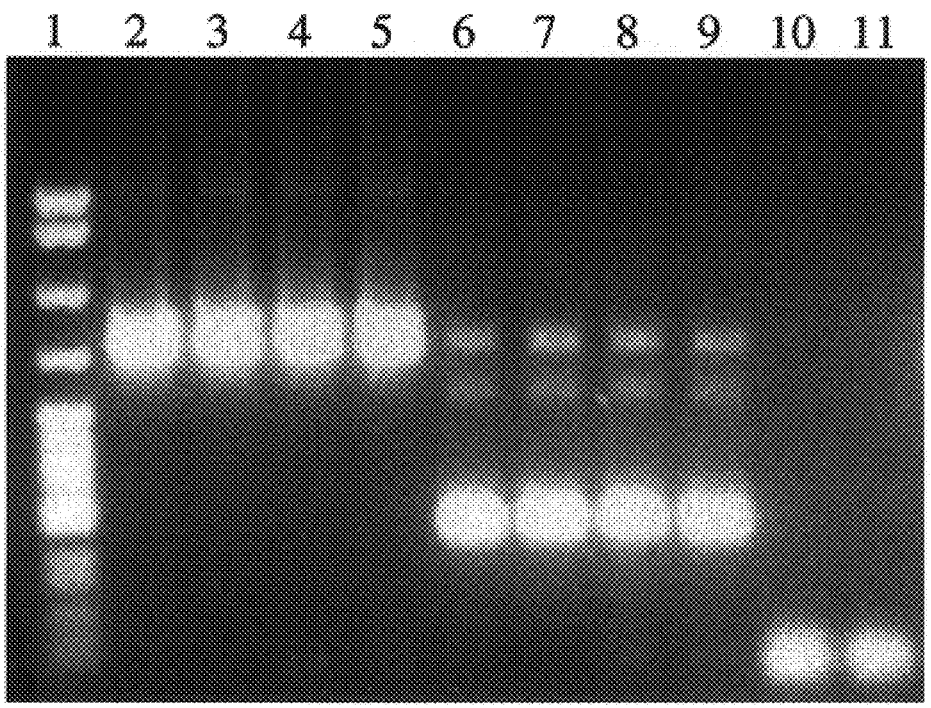
FIG. 1 shows the results of a gel analysis of the hTERT mRNA amplification products generated using primers which flank the β region, as described in Example 2.

To aid in understanding the invention, several terms are defined below.

The term "hTERT protein", as used herein, refers to the catalytic subunit of telomerase.

The terms "hTERT" and "hTERT gene" refer to the genomic nucleic acid sequence that encodes the hTERT protein. The nucleotide sequence of the gene, as used herein, encompasses both coding regions, referred to as exons, and intervening, non-coding regions, referred to as introns.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3):165–187, incorporated herein by reference. Oligonucleotides typically are synthesized using reagents and instruments commercially available from, for example, Perkin Elmer (Norwalk, Conn.) and Pharmacia (Piscataway, N.J.).

The term "hybridization" refers to the formation of a duplex structure by two single stranded nucleic acids due to complementary base pairing. Hybridization can occur between exactly complementary nucleic acid strands or between nucleic acid strands that contain minor regions of mismatch. As used herein, the term "substantially complementary" refers to sequences that are complementary except for minor regions of mismatch, wherein the total number of mismatched nucleotides is no more than about 3 for a sequence about 15 to about 35 nucleotides in length. Conditions under which only exactly complementary nucleic acid strands will hybridize are referred to as "stringent" or "sequence-specific" hybridization conditions. Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. Computer software for calculating duplex stability is commercially available from a variety of vendors.

Stringent, sequence-specific hybridization conditions, under which an oligonucleotide will hybridize only to the exactly complementary target sequence, are well known in the art (see, e.g., Sambrook et al., 1989, *Molecular Cloning—A Laboratory Manual*, Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridizing conditions will allow sequence mismatches to be tolerated; the degree of mismatch tolerated can be controlled by suitable adjustment of the hybridization conditions.

The term "primer" refers to an oligonucleotide capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The primer will contain a "hybridizing region" exactly or substantially complementary to the target sequence. An amplification carried out using the primer in which primer extension is carried out under sufficiently stringent hybridization conditions allows the selective amplification of a specific target sequence. For use in amplification reactions, the primer hybridizing region is preferably from about 15 to about 35 nucleotides in length. A primer oligonucleotide can either consist entirely of the hybridizing region or can contain additional features which allow for the detection, immobilization, or manipulation of the amplified product, but which do not alter the basic property of the primer, that of acting as a point of initiation of DNA synthesis. For example, to facilitate cloning of the amplified product, a short nucleic acid sequence which contains a restriction enzyme cleavage site can be bound to the 5' end of the primer.

The term "probe" refers to an oligonucleotide which is capable of selectively hybridizing to a target nucleic acid under suitable conditions. The probe will contain a "hybridizing region" exactly or substantially complementary to the target sequence, and will be exactly complementary to the target sequence at a polymorphic site. A hybridization assay carried out using the probe under sufficiently stringent hybridization conditions enables the selective detection of a specific target sequence. One of skill in the art will recognize that, in general, the exact complement of a given probe is equally useful as a probe. A probe oligonucleotide can either consist entirely of the hybridizing region or can contain additional features which allow for the detection or immobilization of the probe, but which do not significantly alter the hybridization characteristics of the hybridizing region. For example, the probe hybridizing region may be bound to a poly-T "tail", which is used to immobilize the probe to a solid support for use in the reverse dot-blot assay.

The term "target region" refers to a region of a nucleic acid which is to be analyzed.

Conventional techniques of molecular biology and nucleic acid chemistry, which are within the skill of the art, are fully explained in the literature. See, for example, Sambrook et al., 1989, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); Current Protocols in Human Genetics (Dracopoli et al., eds., 1984 with quarterly updates, John Wiley & Sons, Inc.); and a series, Methods in Enzymology (Academic Press, Inc.), all of which are incorporated herein by reference. All patents, patent applications, and publications mentioned herein, both supra and infra, are incorporated herein by reference.

hTERT Gene Nucleotide Sequence

The nucleotide sequence of the complete coding sequence of the hTERT gene is available from GenBank under accession number AF015950 and is provided below as SEQ ID NO: 1, shown in a 5' to 3' orientation. Although only one strand of the nucleic acid is shown in Table 1, those of skill in the art will recognize that SEQ ID NO: 1 identifies a region of double-stranded genomic nucleic acid, and that the sequences of both strands are fully specified by the sequence information provided. Additionally, those of skill in the art will recognize that the sequence of the expressed mRNA sequence is obtained from the gene sequence provided. As used herein, an hTERT mRNA splice variant corresponding to SEQ ID NO: 1 (i.e., no deletions or insertions) is referred to as a "full-length" mRNA.

hTERT Gene Coding Sequence
(SEQ ID NO:1)

```
   1 gcagcgctgc gtcctgctgc gcacgtggga agccctggcc ccggccaccc ccgcgatgcc
  61 gcgcgctccc cgctgccgag ccgtgcgctc cctgctgcgc agccactacc gcgaggtgct
 121 gccgctggcc acgttcgtgc ggcgcctggg gcccaggggc tggcggctgg tgcagcgcgg
 181 ggaccgggcg gctttccgcg cgctggtggc ccagtgcctg gtgtgcgtgc cctgggacgc
 241 acggccgccc cccgccgccc cctccttccg ccaggtgtcc tgcctgaagg agctggtggc
 301 ccgagtgctg cagaggctgt gcgagcgcgg cgcgaagaac gtgctggcct tcggcttcgc
 361 gctgctggac ggggcccgcg ggggccccccc cgaggccttc accaccagcg tgcgcagcta
 421 cctgcccaac acggtgaccg acgcactgcg ggggagcggg gcgtgggggc tgctgctgcg
 481 ccgcgtgggc gacgacgtgc tggttcacct gctggcacgc tgcgcgctct ttgtgctggt
 541 ggctcccagc tgcgcctacc aggtgtgcgg gccgccgctg taccagctcg gcgctgccac
 601 tcaggcccgg ccccgccac acgctagtgg accccgaagg cgtctgggat gcgaacgggc
 661 ctggaaccat agcgtcaggg aggccgggt cccctgggc ctgccagccc cgggtgcgag
 721 gaggcgcggg ggcagtgcca gccgaagtct gccgttgccc aagaggccca ggcgtggcgc
 781 tgccctgag ccggagcgga cgcccgttgg gcagggtcc tgggcccacc cgggcaggac
 841 gcgtggaccg agtgacgtg gtttctgtgt ggtgtcacct gccagacccg ccgaagaagc
 901 cacctctttg gagggtgcgc tctctggcac gcgccactcc cacccatccg tgggccgcca
 961 gcaccacgcg ggccccccat ccacatcgcg gccaccacgt ccctgggaca cgccttgtcc
1021 cccggtgtac gccgagacca agcacttcct ctactcctca ggcgacaagg agcagctgcg
1081 gccctccttc ctactcagct ctctgaggcc cagcctgact ggcgctcgga ggctcgtgga
1141 gaccatcttt ctgggttcca ggccctggat gccagggact cccgcaggt tgccccgcct
1201 gcccagcgc tactggcaaa tgcggcccct gtttctggag ctgcttggga accacgcgca
1261 gtgccctac ggggtgctcc tcaagacgca ctgcccgctg cgagctgcgg tcaccccagc
1321 agccggtgtc tgtgcccggg agaagcccca gggctctgtg gcggcccccg aggaggagga
1381 cacagacccc cgtcgcctgg tgcagctgct ccgccagcac agcagccct ggcaggtgta
1441 cggcttcgtg cgggcctgcc tgcgccggct ggtgccccca ggcctctggg gctccaggca
1501 caacgaacgc cgcttcctca ggaacaccaa gaagttcatc tccctgggga agcatgccaa
1561 gctctcgctg caggagctga cgtggaagat gagcgtgcgg gactgcgctt ggctgcgcag
1621 gagcccaggg gttggctgtg ttccggccgc agagcaccgt ctgcgtgagg agatcctggc
1681 caagttcctg cactgctga tgagtgtgta cgtcgtcgag ctgctcaggt cttctttta
1741 tgtcacggag accacgtttc aaaagaacag gctcttttc taccgaaga gtgtctggag
1801 caagttgcaa agcattggaa tcagacagca cttgaagagg gtgcagctgc gggagctgtc
1861 ggaagcagag gtcaggcagc atcgggaagc caggcccgcc ctgctgacgt ccagactccg
```

-continued hTERT Gene Coding Sequence
(SEQ ID NO:1)

```
1921 cttcatcccc aagcctgacg ggctgcggcc gattgtgaac atggactacg tcgtgggagc
1991 cagaacgttc cgcagagaaa agagggccga gcgtctcacc tcgagggtga aggcactgtt
2041 cagcgtgctc aactacgagc gggcgcggcg ccccggcctc ctgggcgcct ctgtgctggg
2101 cctggacgat atccacaggg cctggcgcac cttcgtgctg cgtgtgcggg cccaggaccc
2161 gccgcctgag ctgtactttg tcaaggtgga tgtgacgggc gcgtacgaca ccatccccca
2221 ggacaggctc acggaggtca tcgccagcat catcaaaccc cagaacacgt actgcgtgcg
2281 tcggtatgcc gtggtccaga aggccgccca tgggcacgtc cgcaaggcct tcaagagcca
2341 cgtctctacc ttgacagacc tccagccgta catgcgacag ttcgtggctc acctgcagga
2401 gaccagcccg ctgagggatg ccgtcgtcat cgagcagagc tcctccctga atgaggccag
2461 cagtggcctc ttcgacgtct tcctacgctt catgtgccac cacgccgtgc gcatcagggg
2521 caagtcctac gtccagtgcc aggggatccc gcagggctcc atcctctcca cgctgctctg
2581 cagcctgtgc tacggcgaca tggagaacaa gctgtttgcg gggattcggc gggacgggct
2641 gctcctgcgt ttggtggatg atttcttgtt ggtgacacct cacctcaccc acgcgaaaac
2701 cttcctcagg accctggtcc gaggtgtccc tgagtatggc tgcgtggtga acttgcggaa
2761 gacagtggtg aacttccctg tagaagacga ggccctgggt ggcacggctt ttgttcagat
2821 gccggcccac ggcctattcc cctggtgcgg cctgctgctg gatacccgga ccctggaggt
2881 gcagagcgac tactccagct atgcccggac ctccatcaga gccagtctca ccttcaaccg
2941 cggcttcaag gctgggagga acatgcgtcg caaactcttt ggggtcttgc ggctgaagtg
3001 tcacagcctg tttctggatt tgcaggtgaa cagcctccag acggtgtgca ccaacatcta
3061 caagatcctc ctgctgcagg cgtacaggtt tcacgcatgt gtgctgcagc tcccatttca
3121 tcagcaagtt tggaagaacc ccacattttt cctgcgcgtc atctctgaca cggcctccct
3181 ctgctactcc atcctgaaag ccaagaacgc agggatgtcg ctgggggcca agggcgccgc
3241 cggccctctg ccctccgagg ccgtgcagtg gctgtgccac caagcattcc tgctcaagct
3301 gactcgacac cgtgtcacct acgtgccact cctggggtca ctcaggacag cccagacgca
3361 gctgagtcgg aagctcccgg ggacgacgct gactgccctg gaggccgcag ccaaccggc
3421 actgccctca gacttcaaga ccatcctgga ctgatggcca cccgcccaca gccaggccga
3481 gagcagacac cagcagccct gtcacgccgg gctctacgtc ccagggaggg aggggcggcc
3541 cacacccagg cccgcaccgc tgggagtctg aggcctgagt gagtgtttgg ccgaggcctg
3601 catgtccggc tgaaggctga gtgtccggct gaggcctgag cgagtgtcca gccaagggct
3661 gagtgtccga cacacctgcc gtcttcactt ccccacaggc tggcgctcgg ctccacccca
3721 gggccagctt ttcctcacca ggagcccggc ttccactccc cacataggaa tagtccatcc
3781 ccagattcgc cattgttcac ccctcgccct gccctccttt gccttccacc cccaccatcc
3841 aggtgggaac cctgagaagg accctgggag ctctgggaat ttggagtgac caaaggtgtg
3901 ccctgtacac aggcgaggac cctgcacctg gatggggtc cctgtgggtc aaattggggg
3961 gaggtgctgt gggagtaaaa tactgaatat atgagttttt cagttttgaa aaaaa
```

The 16 exons of the hTERT gene correspond to the following nucleotide positions within SEQ ID NO: 1:

| exon | first nucleotide | last nucleotide | size (nucleotides) |
|---|---|---|---|
| exon 1 | 1 | 274 | 274 |
| exon 2 | 275 | 1628 | 1354 |
| exon 3 | 1629 | 1824 | 196 |
| exon 4 | 1825 | 2005 | 181 |
| exon 5 | 2006 | 2185 | 180 |
| exon 6 | 2186 | 2341 | 156 |
| exon 7 | 2342 | 2437 | 96 |
| exon 8 | 2438 | 2523 | 86 |
| exon 9 | 2524 | 2637 | 114 |
| exon 10 | 2638 | 2709 | 72 |
| exon 11 | 2710 | 2898 | 189 |
| exon 12 | 2899 | 3025 | 127 |
| exon 13 | 3026 | 3087 | 62 |
| exon 14 | 3088 | 3212 | 125 |
| exon 15 | 3213 | 3350 | 138 |
| exon 16 | 3351 | 4015 | 665 |

The β-region refers a 182 nucleotide region consisting of exons 7 and 8. A β-region splice variant refers to a splice variant in which exons 7 and 8 are deleted.

Amplification-based Quantitation Methods

In the quantitation methods of the present invention, the hTERT mRNA is amplified using the primers of the invention and the rate or amount of product generated is measured in a manner which allows calculation of the initial target copy number. In preferred embodiments, the amplification is carried out using a polymerase chain reaction (PCR). Amplification by the polymerase chain reaction (PCR), which is now well known in the art, is described in U.S. Pat. Nos. 4,683,195; 4,683,202; and 4,965,188; each incorporated herein by reference. Examples of the numerous articles published describing methods and applications of PCR and, in particular, quantitative PCR, are found in PCR Applications, 1999, (Innis et al., eds., Academic Press, San Diego), PCR Strategies, 1995, (Innis et al., eds., Academic Press, San Diego); and PCR Protocols, 1990, (Innis et al., eds., Academic Press, San Diego), each incorporated herein by reference. Commercial vendors, such as Perkin Elmer (Norwalk, Conn.) market PCR reagents and publish PCR protocols.

Amplification of RNA can be carried out by first reverse-transcribing the target RNA using, for example, a viral reverse transcriptase, and then amplifying the resulting cDNA. In more preferred embodiments, amplification of hTERT mRNA is carried out using a combined high-temperature reverse-transcription-polymerase chain reaction (RT-PCR), as described in U.S. Pat. Nos. 5,310,652; 5,322,770; 5,561,058; 5,641,864; and 5,693,517; each incorporated herein by reference (see also Myers and Sigua, 1995, in PCR Strategies, supra, chapter 5).

Although the polymerase chain reaction is the preferred amplification method, amplification of target sequences in a sample may be accomplished by any known method suitable for amplifying the target sequence described above. Suitable amplification methods include the strand displacement assay (Walker et al., 1992, Proc. Natl. Acad. Sci. USA 89:392–396, Walker et al. 1992, Nucleic Acids Res. 20:1691–1696, and U.S. Pat. No. 5,455,166) and the transcription-based amplification systems, including the methods described in U.S.

Pat. Nos. 5,437,990; 5,409,818; and 5,399,491; the transcription amplification system (TAS) (Kwoh et al., 1989, *Proc. Natl. Acad. Sci. USA* 86:1173–1177); and self-sustained sequence replication (3SR) (Guatelli et al., 1990, *Proc. Natl. Acad. Sci. USA* 87:1874–1878 and WO 92/08800); each of which provides sufficient amplification so that the target sequence can be detected. A review of amplification methods is provided in Abramson and Myers, 1993, *Current Opinion in Biotechnology* 4:41–47, incorporated herein by reference.

Any method for quantitatively detecting the amplified product can be used, including, for example, using fluorescent dyes or labeled probes. Preferred probe-based and-probe-less methods are described below and in the examples.

Probe-based methods are preferred because of the additional specificity obtainable using with probe hybridization. Suitable assay formats for detecting hybrids formed between probes and target nucleic acid sequences in a sample are known in the art-and includes the immobilized target assay formats, such as the dot-blot format, and immobilized probe assay formats, such as the reverse dot-blot assay. Dot blot and reverse dot blot assay formats are described in U.S. Pat. Nos. 5,310,893; 5,451,512; and 5,468,613, each incorporated herein by reference.

In a preferred probe-based method, quantitation is carried out using a "TaqMan" or "5'-nuclease assay", as described in U.S. Pat. Nos. 5,210,015; 5,487,972; and 5,804,375; and Holland et al., 1988, *Proc. Natl. Acad. Sci. USA* 88:7276–7280, each incorporated herein by reference. In the TaqMan assay, labeled detection probes that hybridize within the amplified region are added during the amplification reaction mixture. The probes are modified so as to prevent the probes from acting as primers for DNA synthesis. The amplification is carried out using a DNA polymerase that possesses 5' to 3' exonuclease activity, e.g., Tth DNA polymerase. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product-provides a measure of the synthesis of target sequences.

Any method suitable for quantitatively detecting degradation product can be used in the TaqMan assay. In a preferred method, the detection probes are labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification.

An alternative, probe-less method, referred to herein as a kinetic-PCR method, for measuring the increase in amplified nucleic acid by monitoring the increase in the total amount of double-stranded DNA in the reaction mixture is described in Higuchi et al., 1992, *Bio/Technology* 10:413–417; Higuchi el al., 1993, *Bio/Technology* 11:1026–1030; Higuchi and Watson, in PCR Applications, supra, Chapter 16; U.S. Pat. No. 5,994,056; and European Patent Publication Nos. 487, 218 and 512,334, each incorporated herein by reference. The detection of double-stranded target DNA relies on the increased fluorescence that ethidium bromide (EtBr) and other DNA-binding dyes exhibit when bound to double-stranded DNA. The increase of double-stranded DNA resulting from the synthesis of target sequences results in an increase in the amount of dye bound to double-stranded DNA and a concomitant detectable increase in fluorescence.

Quantitation of a sample containing an unknown number of target sequences typically is carried out with reference to a "standard curve" generated from a series of amplifications of samples containing the target sequence in a range of known amounts. The standard curve is used to calculate an input copy number from the signal generated during an amplification. Thus, the unknown target sequence copy number in the sample of interest is estimated using the standard curve by calculating the copy number that previously was determined to yield a signal equal to that observed. The concentration of the target sequence in the sample then is calculated from the input copy number and the sample size, which is determined prior to the reaction.

Quantitative estimates can be sensitive to variability in either the input sample size or in the reaction efficiency. The effect of inter-reaction variability of the input sample size on the calculated hTERT concentration can be eliminated by using a control gene. As described in the examples, a control gene is selected which provides an independent measure of the amount of RNA in the sample. The calculated concentration of hTERT mRNA is adjusted based on the independent measure of sample size.

Variability in the amplification efficiency between the reactions used to generate the standard curve and the reaction used to assay the sample of interest can affect the applicability of the standard curve. Carrying out the reactions used to generate the standard curve simultaneously with the reaction used to assay the sample of interest, using the same "master mix" of amplification reagents, and, preferably, in adjacent wells in the same thermal cycler, will minimize the inter-reaction variation in efficiency. Alternatively, an internal standard can be used to adjust the results to account for variation in amplification efficiency.

The effect of inter-reaction variability of reaction efficiency between the reactions used to generate the standard curve and the reaction used to assay the sample of interest can be eliminated by using an internal standard. The internal standard is added to reaction in a known copy number and co-amplified along with the hTERT mRNA target. The signal generated from the known amount of the internal standard provides an indication of the overall reaction efficiency which can be used to adjust the estimated copy number to account for the difference in reaction efficiencies.

Amplification-based quantitation methods using an internal standard are described in U.S. Pat. Nos. 5,219,727 and 5,476,774, and in Wang and Mark, 1990, in PCR Protocols, supra, each incorporated herein by reference. The internal standard is an nucleotide sequence that contains the same primer binding sites present in the target such that it is amplified by the same primer pair, but is distinguishable from the target sequence either by length or, preferably, by the presence of a unique internal sequence. The internal standard is included in a known copy number amplifications of the sample of interest and is amplified with approximately the same efficiency as the target sequence. Any change in the signal generated by amplification of the internal standard relative to the signal expected from the standard curve reflects a change in the overall reaction efficiency and is used to adjust the estimate of the target sequence copy number correspondingly.

Amplification reaction mixtures are typically assembled at room temperature, well below the temperature needed to insure primer hybridization specificity. Non-specific amplification may result because at room temperature the primers may bind non-specifically to other, only partially complementary nucleic acid sequences, and initiate the synthesis of undesired nucleic acid sequences. These newly synthesized, undesired sequences can compete with the desired target sequence during the amplification reaction and can significantly decrease the amplification efficiency of the desired sequence.

A variety of methods have been described for increasing the specificity of an amplification reaction; preferred methods are described in European Patent application No. 0 866,071 and co-pending U.S. application Ser. No. 09/039, 866, both incorporated herein by reference. As described therein, one or both of the amplification primers can be modified by the covalent attachment of a modifier group to the exocyclic amine of a nucleotide at or near the 3' terminus.

Sample preparation methods suitable for the amplification of RNA are well known in the art and fully described in the literature cited herein. The particular method used is not a critical part of the present invention. Examples of suitable methods are described in the examples. One of skill in the art can optimize reaction conditions for use with the known sample preparation methods.

Amplification Primers

In the methods of the present invention, a target region is amplified using a pair of primers comprising a primer that hybridizes within exon 8 and a primer that hybridizes either upstream of exon 7 or downstream of exon 8. The use of such primers provides improved specificity for hTERT mRNA that encodes an active hTERT protein and thereby improves estimates of telomerase activity based on the level of hTERT mRNA expression. Primer pairs that satisfy the requisite hybridization criteria are designed based on the sequence provided as SEQ ID NO: 1.

Preferably, a target region is amplified using a pair of primers comprising a primer that hybridizes within exon 8 and a primer that hybridizes upstream of exon 7. We have discovered that the use of a primer that hybridizes upstream of exon 7 along with a primer that hybridizes within exon 8 is more likely to provide a particularly efficient amplification of hTERT mRNA.

A particularly preferred pair of primers consists of upstream primer, SYC1118 (SEQ ID NO: 5), which hybridizes to a sequence within exon 6 at positions 2311–2325, and downstream primer, SYC1097 (SEQ ID NO: 4), which hybridizes to a sequence within exon 8 at positions 2489–2506. The nucleotide sequences of these primers are provided in the examples. These primers enable the particularly efficient and specific amplification of hTERT mRNA. The specificity of these primers is advantageous in a quantitative assay because it eliminates any competitive inhibition resulting from the amplification of non-target sequence resulting from the mispriming of the primers on related sequences. Similarly, the preferred primer pair typically minimize the formation of template-independent non-specific amplification products, known as primer dimer.

Probes

In one embodiment of the present invention, the amplified nucleic acid sequence is detected by hybridization under suitably stringent hybridization conditions with a labeled oligonucleotide probe. The particular probe sequence is not a critical aspect of, the invention. The design of probes specific for a particular target sequence and suitable for use in a particular assay format is well known in the art.

For use in the TaqMan assay format described herein, suitable oligonucleotides probes preferably are from about 15 to about 50 nucleotides in length, more preferably about 25 to about 35 nucleotides in length. The Tm of the probe-target sequence hybridization duplex preferably is about 5° C. to about 10° C. higher than the Tm's of the primer-target sequence hybridization duplexes. In other probe-based assay formats, significantly longer probes also can be used. A probe comprises (or consists of) a region that is exactly or substantially complementary to the hTERT mRNA sequence within the amplified region.

In a preferred embodiment, the probe hybridizes to a region which encompasses at least a portion of exon 7, more preferably a region which encompasses the exon 7–exon 8 splice junction. The use of such a probe enables discrimination of a splice variant corresponding to a deletion of exon 7 only. Although this particular splice variant has not been observed, the use of a probe capable of discriminating against such a splice variant provides additional assurance that the mRNA measured corresponds to an active hTERT.

Particularly preferred probe sequences are described in the examples. It will be understood that the complement of a probe typically is also useful as a probe.

The probe-based assay formats described above typically utilize labeled oligonucleotides to facilitate detection. Oligonucleotides can be labeled by incorporating a label detectable by spectroscopic, photochemical, biochemical, immunochemical, or chemical means. Useful labels include radioactive labels, such as $^{32}$P, fluorescent dyes, electron-dense reagents, enzymes (as commonly used in ELISAS), biotin, or haptens and proteins for which antisera or monoclonal antibodies are available. Labeled oligonucleotides of the invention can be synthesized and labeled using the techniques described above for synthesizing oligonucleotides.

Kits

The present invention also relates to kits comprising useful components for practicing the present method. A useful kit can contain oligonucleotide primers and, optionally, probes specific for the targets regions of the hTERT mRNA described herein. Other optional components of the kit include, for example, an agent to catalyze the synthesis of primer extension products, the substrate nucleoside triphosphates, means used to label (for example, an avidin-enzyme conjugate and enzyme substrate and chromogen if the label is biotin), the appropriate buffers for PCR or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Sample Preparation Protocols for hTERT mRNA Quantitation

The following protocols are suitable for the preparation of total RNA from human samples for use in hTERT mRNA quantitation.

Following preparation, the total RNA concentration in the sample typically is determined by measuring the optical density at a wavelength of 260 nanometers ($OD_{260}$) following standard protocols. Alternatively, the total RNA concentration in the sample can be determined using the RiboGreen™ Quantitation Kit (Molecular Probes, Eugene, Oreg.). The sample is diluted to the desired concentration prior to amplification. In the amplifications describe herein, preferably about 100 to 200 ng of total RNA is used. The quantity of total RNA from clinical specimens such as from urine may be difficult to ascertain initially. Methods of estimating the total RNA concentration in the sample by using another gene as a standard are described below.

A. Cell Lines

Total RNA can be prepared from cell lines using RNAzol™ from Tel-Test, Inc. (Friendswood, Tex.). The following example protocol is suitable for a sample comprising approximately $10^7$ cells.

1) Resuspend in 2 ml of RNAzol™, homogenize
2) Add 0.2 ml chloroform, shake vigorously for 15 sec, incubate on ice for 5 min.
3) Centrifuge at 12,000 g for 15 min at 4° C.
4) Transfer the aqueous phase to a fresh tube
5) Add an equal volume of isopropanol and store at 4° C. for 15 min
6) Centrifuge at 12,000 g for 15 min at 4° C.
7) Remove supernatant
8) Add 1 ml 70% ethanol to the pellet
9) Centrifuge at 12,000 g for 15 min at 4° C.
10) Remove supernatant completely
11) Dry the pellet briefly
12) Resuspend in Rnase free $H_2O$ B. Tissues Total RNA can be prepared from tissues using the High Pure™ RNA Tissue Kit (Roche Molecular Biochemicals, Indianapolis, Ind.) following the manufacturer's protocols.

C. Urine

1) Collect 50 ml urine
2) Centrifuge at 1,000 g for 10 min at room temperature immediately
3) Remove supernatant with a pipette completely and carefully without disturbing the pellet
4) Add $\leq$50 ml PBS (Phosphate Buffered Saline, Dulbecco's without $Ca^{++}$ and $Mg^{++}$, sterile, room temperature) to the pellet
5) Mix gently (do not vortex)
6) Centrifuge at 1,000 g for 10 min at room temperature
7) Remove supernatant with a pipette carefully
8) Leave 1 to 1.5 ml of PBS in the tube,
9) Mix gently (do not vortex)
10) Transfer the suspension to a 1.5 ml Eppendorf tube
11) Centrifuge at 1,000 g (3,500 rpm with Eppendorf Microfuge) for 2 min at room temperature
12) Remove supernatant with a pipette completely and carefully without disturbing the pellet
13) Resuspend the pellet in 200 µl PBS and add 400 µl High Pure lysis buffer
14) Mix with pipette tip gently
15) Store at −70° C. immediately
16) Use High Pure™ RNA Isolation Kit (Roche Molecular Biochemicals, Indianapolis, Ind.) to prepare total RNA

EXAMPLE 2

Identification of a New Splice Variant

A previously unobserved splice variant was identified by amplifying hTERT mRNA using primers that flank the p region and analyzing the amplified product by gel electrophoreses.

Samples

Amplifications were carried out using the following samples:

1. A dilution series of hTERT positive control mRNA, prepared from a transcription plasmid containing the entire hTERT gene coding sequence.
2. Total RNA from human thymus cells, purchased from Clonetech (Palo Alto, Calif.).
3. Total RNA from a leukemia cell line (K562), prepared according to the protocol described in Example 1.

Amplification Primers

Amplification of a region of the hTERT mRNA was carried out using the following primers, shown in the 5' to 3' orientation: p1 SYC1076 (SEQ ID NO: 2) 5'-CATGGGCACGTCCGCAA-3'

SYC1078 (SEQ ID NO: 3) 5'-CGCCGAATCCCCGCAAA-3'

The upstream primer, SYC1076 (SEQ ID NO: 2), hybridizes to a sequence within exon 6 at positions 2309–2325. The downstream primer, SYC1078 (SEQ ID NO: 3), hybridizes to a sequence within exon 9 at position 2615–2631. Together, these primers catalyze the amplification of a 323 nucleotide product encompassing the β region from the full length hTERT mRNA sequence.

Amplification

Each PCR amplification was carried out in a total reaction volume of 100 µl. The final reagent concentrations were as follows:

100 ng sample RNA
50 mM Bicine, pH 8.2
125 mM KOAc
8% glycerol
4 mM $Mn(OAc)_2$
200 µM dATP, dGTP, dCTP
400 µM dUTP
200 nM each primer
1 µg/ml ethidium bromide
2 units UNG*
10 units rTth DNA polymerase*

* developed and manufactured by Hoffmann-La Roche and commercially available from Perkin Elmer (Norwalk, Conn.).

Amplification reactions were carried out in a GeneAmp PCR system 9600 thermal cycler (Perkin Elmer, Norwalk, Conn.), using the specific temperature cycling profile used is shown below.

| Thermal Cycling Times and Temperatures | |
| --- | --- |
| Pre-reaction incubation: | 50° C. for 2 minutes |
| | 95° C. for 1 minute |
| Reverse-transcription | 62° C. for 30 minutes |
| 60 cycles: | |
| denature: | 95° C. for 20 seconds |
| anneal/extend: | 60° C. for 30 seconds |
| Final extension and hold: | 72° C. |

Gel Electrophoretic Detection

Amplification reaction products (5 µl) were analyzed by agarose gel electrophoresis. A 3% Nusieve GTG and 0.5% Agarose (FMC Bio Products, Rockland, Me.) gel containing 0.5 µg/ml ethidium bromide (Cal Biochem, La Jolla, Calif.) was used with a 1×TBE (89 mM Tris-borate and 2.5 mM disodium EDTA, pH 8.3) running buffer containing 0.5 µg/ml ethidium bromide. Electrophoresis was carried out at 100 volts for approximately 1 hour. The gel was destained briefly in water and the ethidium bromide-stained bands of DNA were visualized using UV irradiation.

A pBR322/Msp1-digested Ladder (New England Biolabs, Beverly, Mass.) was included in a separate lane as a size marker.

Results

The results are shown in FIG. 1. The lane assignments are provided in the table below.

| Lane No. | Sample |
| --- | --- |
| 1 | pBR322/Msp1-digested Ladder |
| 2, 3 | 2 × 10⁶ copy hTERT positive control RNA |
| 4, 5 | 2 × 10⁵ copy hTERT positive control RNA |
| 6, 7 | 100 ng thymus RNA |
| 8, 9 | 100 ng K562 RNA |
| 10, 11 | No-template control |

Amplification of the positive control mRNA, which contains the entire hTERT coding sequence, resulted in a single amplification product, as seen in lanes 2–5.

Amplifications from the thymus, lanes 6–7, and K562, lanes 8–9, resulted in three specific bands corresponding to splice variants of hTERT mRNA of three different sizes. The largest product observed resulted from the amplification of a full-length hTERT mRNA splice variant, as can be seen by comparison with the amplified product in lanes 2–5. The smallest product corresponds to the 141 nucleotide product expected from the amplification of a β-deleted splice variant. The intermediate band resulted from the amplification of a previously unseen splice variant. The size of the band corresponds to a product in which exon 7 is deleted.

Amplifications of the no-template control did not result in an amplification product other than the production of some primer-dimer.

As seen in lanes 6–9, an estimate of telomerase activity based on a quantitation of hTERT mRNA expression would be inaccurate because only a fraction of the mRNA in the sample encodes an active hTERT protein. Furthermore, the smallest product, corresponding to the β-deletion splice variant, is amplified most efficiently and competitively inhibits the amplification of the larger two fragments, including the mRNA which encodes an active hTERT protein. Because of this competition, a method of quantitating hTERT mRNA expression by amplifying as above and then selectively measuring only the amount of product generated from the full-length mRNA, either by gel analysis or appropriate probe analysis, would provide an unreliable measure of the mRNA which encodes an active hTERT protein. This unpredictability can be eliminated by selectively amplifying only hTERT mRNA that encodes an active hTERT protein, as described in the following examples.

EXAMPLE 3

Selective Amplification of mRNA that Encodes an Active hTERT Protein

Selective amplification of mRNA that encodes an active hTERT protein was carried out using primers that hybridized to regions within exon 6 and exon 8, respectively, as described below.

Samples:

Amplifications were carried out using the following samples:

1. A dilution series of hTERT positive control mRNA
2. 100 ng total RNA from a prostate carcinoma cell line (LNCaP), prepared as described in Example 1.
3. 100 ng total RNA from a leukemia cell line (K562), prepared as described in Example 1.
4. 100 ng total RNA from human thymus cells (Clonetech (Palo Alto, Calif.)).

Amplification Primers

Amplification of a region of the hTERT mRNA was carried out using upstream primer SYC1076 (SEQ ID NO: 2), described above, together with the following downstream primer, shown in the 5' to 3' orientation:

SYC1097 (SEQ ID NO: 4) 5'-GGCGTGGTGGCACATGAA-3'

The upstream primer, SYC1076 (SEQ ID NO: 2), hybridizes to a sequence within exon 6 at positions 2309–2325. The downstream primer, SYC1097 (SEQ ID NO: 4), hybridizes to a sequence within exon 8 at positions 2489–2506. Together, these primers catalyze the amplification of a 198 nucleotide product from the full length hTERT mRNA sequence.

Amplification and Gel Analysis

Amplifications were carried out as described in Example 2, except that 3 mM Mn(OAc)₂ was used in the reaction mixture and the reverse transcription was carried out at 60° C. The reaction products were analyzed as described in Example 2, with the additional inclusion of a second size ladder (100 base-pair ladder, Life Technologies, Rockville, Md.) in a separate lane of the gel.

Figure 2:
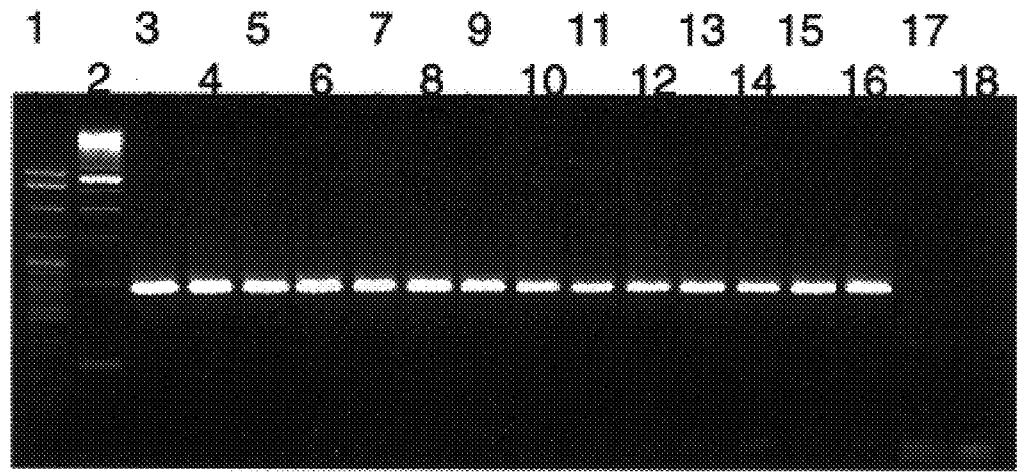
FIG. 2 shows the results of a gel analysis of the hTERT mRNA amplification products generated using primers of the present invention, as described in Example 3.

Results:

The results are shown in FIG. 2. The lane assignments are provided in the table below.

| Lane | Sample |
| --- | --- |
| 1 | pBR322/Msp1-digested ladder |
| 2 | 100 base-pair ladder |
| 3, 4 | 2 × 10⁶ copy hTERT positive control RNA |
| 5, 6 | 2 × 10⁵ copy hTERT positive control RNA |
| 7, 8 | 2 × 10⁴ copy hTERT positive control RNA |
| 9, 10 | 2 × 10³ copy hTERT positive control RNA |
| 11, 12 | 100 ng LNCaP RNA |
| 13, 14 | 100 ng K562 RNA |
| 15, 16 | 100 ng thymus RNA |
| 17, 18 | No-template control |

As seen in lanes 3–14, amplifications from all samples resulted in a single product corresponding to the expected 198 nucleotide product.

The reactions described herein, and in Example 2, were carried out essentially until the reaction reached a plateau in product accumulation. Therefore, rather than provide a quantitative estimate of the initial target number, the amount of product obtained would be expected to be relatively constant regardless of the input target number unless inhibition occurs by, for example, the competitive amplification of another target. The effects of the competitive inhibition on the amplification of full-length hTERT mRNA by the preferential amplification of the small, β-deletion splice variant can be seen in FIG. 1 by comparing the band intensities corresponding to the full-length hTERT mRNA in lanes 2–5 with those in lanes 6–9. In contrast, the essentially uniform band intensities seen in FIG. 2 from the amplifications of full-length mRNA corresponding to an active hTERT protein indicate a lack of competitive inhibition. The uniform amplification efficiency obtained-using the primers of the invention, even from samples which contain short splice variants, demonstrates an advantage of the primers and methods of the present invention. This uniformity provided by the primers of the invention results in more consistent and accurate quantitative estimates when used in the quantitative methods described in the following examples.

EXAMPLE 4

Quantitation of hTERT mRNA: TagMan Format

This example describes quantitation of hTERT mRNA in a TaqMan format.

Samples

Amplifications were carried out using the samples described below. All samples were prepared as described in Example 1.

1. A dilution series of hTERT positive control mRNA
2. 200 ng total RNA from a HT1080 cell line
3. 200 ng total RNA from a HeLa cell line
4. 200 ng total RNA from a HuVec cell line
5. 200 ng total RNA from a SW480 cell line
6. 200 ng total RNA from a LNCaP cell line
7. 200 ng total RNA from a kidney 293 cell line
8. 200 ng total RNA from a K562 cell line
9. 200 ng total RNA from a WIN cell line The cell line samples are from well known immortal cell lines known to express telomerase activity with the exception of WIN cell line, which is an immortal cell line known to lack telomerase activity.

Amplification Primers and Detection Probe

Amplification of a region of the hTERT mRNA was carried out using the following upstream primer, shown in the 5' to 3' orientation, together with downstream primer SYC1097 (SEQ ID NO: 4), described above:

SYC1118 (SEQ ID NO: 5) 5'-TGGGCACGTCCGCAA-3'

The upstream primer, SYC1118 (SEQ ID NO: 5), hybridizes to a sequence within exon 6 at positions 2311–2325. The downstream primer, SYC1097 (SEQ ID NO: 4), hybridizes to a sequence within exon 8 at positions 2489–2506. Together, these primers catalyze the amplification of a 196 base pair product encompassing the β region from the full length hTERT mRNA sequence.

The 3' terminal nucleotide of SYC1118 (SEQ ID NO: 5) was modified by the covalent attachment of a p-tert-butylbenzyl group to the 3' terminal nucleotide, as described in European Patent Application No. 866,071, incorporated herein by reference.

Detection was carried out using CS12 (SEQ ID NO: 6), shown below in the 5' to 3' orientation. This probe hybridizes to the hTERT gene sequence at positions 2427–2456, which spans the splice junction between exons 7 and 8.

CS12 (SEQ ID NO: 6)
5'-TCATCGAGCAGAGCTCCTCCCTGAATGAGG-3'

To enable detection in the TaqMan format, the probe was labeled with two fluorescent dyes. The probe was synthesized to contain a Cy5 flurophore attached to the 5' terminus through the terminal phosphate using the commercially available phosphoramidite (Pharmacia, Piscataway, N.J.). A fluorescein (FAM) label was incorporated in an internal position between nucleotides 8 and 9 using a labeled linker commercially available as a phosphormaidite from Bio-Genex (San Ramon, Calif.). The resulting probes are self-quenching when in an unhybridized state. To prevent extension of the probe by the DNA polymerase during the amplification, the probe was synthesized with a 3' phosphate block using a phosphoramidite commercially available from Glenn Research (Sterling, Va.).

Alternatively, either of the following probes can be used, labeled and modified as described above:

CS1 (SEQ ID NO: 7)
5'-CAGCAGTGGCCTCTTCGACGTCTTCCTACG-3'

CS3 (SEQ ID NO: 8)
5'-TCTACCTTGACAGACCTCCAGCCGTACATG-3'

Amplification

Each PCR amplification was carried out in a total reaction volume of 100 μl. The final reagent concentrations were as follows:

sample RNA
50 mM Bicine, pH 8.2
125 mM KOAc
8% glycerol
3 mM Mn(OAc)$_2$
200 μM dATP, dGTP, dCTP
400 μM dUTP
200 nM each primer
100 nM probe
1% DMSO
2 units UNG*
10 units rTth DNA polymerase*

* developed and manufactured by Hoffmann-La Roche and commercially available from Perkin Elmer (Norwalk, Conn.).

Preferably, 1% DMSO is added to the reaction mixture. The ethidium bromide was included in the reaction to facilitate gel analysis and, in general, can be omitted.

Amplification reactions were carried out in a GeneAmp® 5700 Sequence Detection System (PE Biosystems, Foster City, Calif.), using the specific temperature cycling profile used is shown below.

| Thermal Cycling Times and Temperatures | |
|---|---|
| Pre-reaction incubation: | 50° C. for 2 minutes |
| | 95° C. for 1 minute |
| Reverse-transcription | 60° C. for 30 minutes |
| 60 cycles: | |
| denature: | 95° C. for 20 seconds |

-continued

| Thermal Cycling Times and Temperatures | |
|---|---|
| anneal/extend: | 60° C. for 30 seconds |
| Final extension and hold: | 72° C. |

Quantitative TagMan Analysis

In a TaqMan reaction, the 5' to 3' exonuclease activity of the DNA polymerase cleaves probes hybridized to the target sequence during amplification, thereby releasing labeled probe fragments into the reaction mixture. Cleavage of the probe, which is self-quenching in its intact state, results in separation of the quencher and fluorophore and an increase in the fluorophore fluorescence.

The accumulation of amplified product was measured at each cycle during the reaction by measuring the increase in reaction fluorescence. During each amplification cycle, the probes are excited with light at a wavelength near the excitation maximum of the fluorophore and the emission of the fluorophore is measured near its emission maximum. These frequencies are pre-determined in a GeneAmp® 5700 Sequence Detection System; if another thermal cycler were used, appropriate frequencies should be selected.

Fluorescence measurements were-normalized by dividing by an initial fluorescence measurement obtained during a cycle early in the reaction while the fluorescence measurements between cycles appear to be relatively constant. The cycle number chosen for the initial fluorescence measurement was the same for all reactions compared, so that all measurements represent increases relative to the same reaction cycle.

To quantify the differences among the reactions, the results were expressed in terms of the number of amplification cycles carried out until the fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. During the geometric growth phase of the amplification, the number of cycles required to reach a particular threshold value is proportional to the logarithm of the initial target copy number. Accumulation of amplified product in later cycles inhibits the reaction and eventually leads to a reaction plateau.

An AFL of 1.12 was chosen for all reactions. Because a PCR amplification consists of discrete cycles and the fluorescence measurements are carried out once per cycle, the measured fluorescence typically increases from below the AFL to above the AFL in a single cycle. To improve the precision of the measurements, an "exact" number of cycles to reach the AFL threshold, referred to herein as the $C_T$ value, was calculated by interpolating fluorescence measurements between cycles.

Results:

The $C_T$ values obtained for each of the samples are shown in the tables, below. Each of the $C_T$ values represents the average value obtained from two reactions, with the exception of the amplification of the 10-copy control. Only one of the two replicate amplifications of the 10-copy control resulted in a detectable product. Gel analysis of the amplification products (not shown), carried out separately as described above, indicated that the second reaction generated product corresponding to primer dimer. The lack of product in the second 10-copy reaction could have resulted either from an actual lack of target in the initial sample due to inaccuracy in estimating the target copy number, or from the competitive amplification of primer-dimer.

| Sample | $C_T$ value |
|---|---|
| Control Samples | |
| $10^5$ copy hTERT positive control | 26.83 |
| $10^4$ copy hTERT positive control | 30.15 |
| $10^3$ copy hTERT positive control | 33.57 |
| $10^2$ copy hTERT positive control | 36.84 |
| 10 copy hTERT positive control | 41.28 |
| Human Cell-line Samples | |
| 200 ng HT1080 cell line | 30.95 |
| 200 ng HeLa cell line | 34.53 |
| 200 ng HuVec cell line | 39.35 |
| 200 ng SW480 cell line | 33.36 |
| 200 ng LNCaP cell line | 31.68 |
| 200 ng 293 cell line | 31.01 |
| 200 ng K562 cell line | 32.58 |
| 200 ng WIN cell line | — |

A standard curve was derived from the $C_T$ values obtained from amplifications of known amounts of hTERT mRNA positive control template. A standard curve is obtained, for example, by fitting the data to a linear equation expressing the relationship between the logarithm of the input copy number and the $C_T$. Specifically, the data were fit to the following equation:

$$\text{Log}(N_0) = \text{Log}(N_{AFL}) - \text{Log}(R) * C_T,$$

where $N_0$ is the initial copy number, $N_{AFL}$ is a constant equal to the copy number corresponding to the AFL, R is a constant equal to the efficiency of each amplification cycle, and Log(X) is the logarithm base 10 of X. Algorithms for fitting data to a linear equation, such as by the least squares method, are well known and included in many statistical software packages and spreadsheet programs.

From the $C_T$ values obtained from the control samples, the following standard curve was obtained:

$$\text{Log}(N_0) = 44.411 - 3.559 * C_T$$

Calculation of the input copy number for each of the cell-line samples was carried out using the standard curve generated from the known control templates. Typically, the mRNA concentration is the quantity of interest, which is obtained by dividing the calculated copy number by the sample size.

Using the above standard curve, hTERT mRNA concentrations (copies of hTERT mRNA per ng of total RNA) were calculated for each of the tissue samples. The results are shown below.

| Calculated hTERT concentrations (copies/ng) | |
|---|---|
| Sample | HTERT concentration |
| 200 ng HT1080 cell line | 29.81 |
| 200 ng HeLa cell line | 2.87 |
| 200 ng HuVec cell line | 0.13 |
| 200 ng SW480 cell line | 6.13 |
| 200 ng LNCaP cell line | 18.46 |
| 200 ng 293 cell line | 28.65 |
| 200 ng K562 cell line | 10.26 |
| 200 ng WIN cell line | 0.00 |

Corrections for Sample RNA Quantity Variability

The accuracy of the calculated hTERT mRNA concentration is sensitive to the accuracy of measurement of the total RNA used in the assay. Inter-sample variability in input total RNA will result in increased variability of the calculated concentrations, which will tend to weaken the statistical significance of the correlation with telomerase activity. Typically, and as described above, the total amount of RNA used in a reaction is measured based on the optical density of the RNA sample. This also provides a relevant measure of number of cells in the sample because the total amount of RNA per cell is known to be relatively constant. To maximize the precision of the hTERT mRNA quantitation, a more precise quantitative measurement of total RNA than possible by optical density is desirable. In addition, it may not be feasible to measure the total amount of RNA by optical density prior to running the assay, particularly using clinical samples, if only a small quantity of sample is available.

The estimate of the amount of total RNA in the sample can be improved by separately measuring the expression of another gene which is expressed at a constant level in all cells of that tissue type as a control. The estimate of total RNA then is adjusted based on the measured expression of the control gene relative to the expected expression. Equivalently, the measured hTERT mRNA concentration is adjusted based on the measured expression of the control gene relative to the expected expression.

The choice of a suitable control gene is not a critical aspect of the invention. A suitable control gene is one that is expressed at a constant, measurable level in both normal and cancerous cells. Candidate genes are known in the literature and can be screened empirically in a routine manner. Typically, candidate genes are selected from the "housekeeping" genes, whose expression products are essential to the basic metabolism of the cell and are expressed at a moderate or high, constant level. One particular example is described herein.

The control gene mRNA copy number typically is quantitated in a separate reaction using an aliquot of the sample used to measure the hTERT mRNA copy number. However, the quantitation of both mRNA's also can be carried out in a single reaction using, for example, probes labeled with distinguishable dyes.

After calculating the control gene mRNA copy number, the measured amount of total RNA can be adjusted to provide as more accurate value according to the following:

adjusted total RNA=measured total RNA*(control #)/(expected control #), where the measured total RNA refers to the initial value obtain from the optical density, (control #) is the measured control gene mRNA copy number, and (expected control #) is the number of control gene mRNA copies expected in a sample of the original sample size. Equivalently, an adjusted hTERT mRNA concentration is calculated according to the following:

adjusted [hTERT]=[hTERT]*(expected control #)/(control #), where [hTERT] refers to the hTERT mRNA concentration.

Preferably, a separate standard curve for use in quantitating the housekeeping gene expression is produced from a series of samples of known copy number. However, if the amplification efficiency of the hTERT mRNA and the control gene mRNA are similar, the hTERT mRNA standard curve can be used to quantitate the control mRNA. As a result, the estimated copy number typically will differ from an estimate that would be obtained using a standard curve generated from the control gene expression by a constant multiplicative factor. However, because both the expected control value and the measured control value will differ from their "correct" values by the same multiplicative factor, the ratio used in adjusting the hTERT mRNA concentration is unchanged. The amplification efficiency of the control reactions can be matched to the hTERT amplification efficiency by selecting primers which amplify a region of similar size and screening primers pairs for efficient amplification.

The calculated hTERT concentrations were adjusted based on the expression of the housekeeping gene, EF1A (Elongation Factor 1-α). Preliminary screening indicated that EF1A is expressed at a relatively constant level in both normal and cancerous tissue samples.

The EF1A mRNA sequence is available from GenBank under accession no. X03558. The primers used to amplify a region of the EF1A are provided below, shown in the 5' to 3' orientation:

HA300 (SEQ ID NO: 9) 5'-CAATGCCAGTGGAACCA-3'

HA299 (SEQ ID NO: 10) 5'-CCATACCGGGTTTGAGAACA-3'

Quantitation of the EF1A mRNA was carried out using the probe-less kinetic PCR methods described in Example 6, below, using the conditions described therein, but with the above primers. The standard curve generated from the hTERT controls was used to calculate the EF1A copy number. The expected EF1A copy number was estimated as the average copy number observed in each of the reactions.

The adjusted hTERT concentrations (copies of hTERT mRNA per ng of total RNA) are shown in the table, below.

| Adjusted hTERT concentrations (copies/ng) | |
|---|---|
| Sample | hTERT concentration |
| 200 ng HT1080 cell line | 25.35 |
| 200 ng HeLa cell line | 7.38 |
| 200 ng HuVec cell line | 0.22 |
| 200 ng SW480 cell line | 7.23 |
| 200 ng LNCaP cell line | 16.28 |
| 200 ng 293 cell line | 38.34 |
| 200 ng K562 cell line | 9.16 |
| 200 ng WIN cell line | 0.00 |

EXAMPLE 5

Estimation of Teleomerase Activity

The utility of using the hTERT mRNA expression to estimate telomerase activity was investigated using the samples described in the previous example. The samples used to measure the telomerase activity were aliquots of the same cell line samples used in the previous example to measure the hTERT mRNA concentration. The adjusted hTERT mRNA concentrations are reported in the previous example.

Telomerase activity present in the samples was assayed using the kinetic TRAP assay described in Chang, 1999, in PCR Applications (Innis et al., eds.) Chapter 17, Academic Press, San Diego, incorporated herein by reference.

In the TRAP assay, as described in U.S. Pat. No. 5,629, 154, incorporated herein by reference, a telomerase substrate that lacks a telomerase repeat unit is added to an aliquot of a cell extract in an appropriate buffer. Telomerase activity present in the cell extract results in the addition of telomerase repeat units to the substrate. The extended substrate subsequently is detected by amplifying with a primer pair consisting of a first primer specific for the repeat unit and a second primer that is an excess of the telomerase substrate, and analyzing the amplified product by gel electrophoresis.

The kinetic TRAP assay, as described in Chang, 1999, supra, is a quantitative version of the TRAP assay in which the amplification of the extended telomerase substrate is carried out using the kinetic PCR methods described in Higuchi and Watson, 1999, supra (also see below), which enable a quantitative measure of the telomerase substrate extended by the telomerase. The initial telomerase extension reaction is carried out for 10 minutes at 25° C. To calibrate the results, a standard curve is generated from separate amplifications of a dilution series of a synthetic template using the same primers. The $C_T$ value obtained from the amplification of the extended telomerase substrate is used to calculate an initial copy number of synthetic template (or, equivalently, concentration) which would result in the same $C_T$ value. Thus, the kinetic TRAP assay provides a quantitative measure of telomerase activity expressed as an initial concentration of synthetic template.

Figure 3:
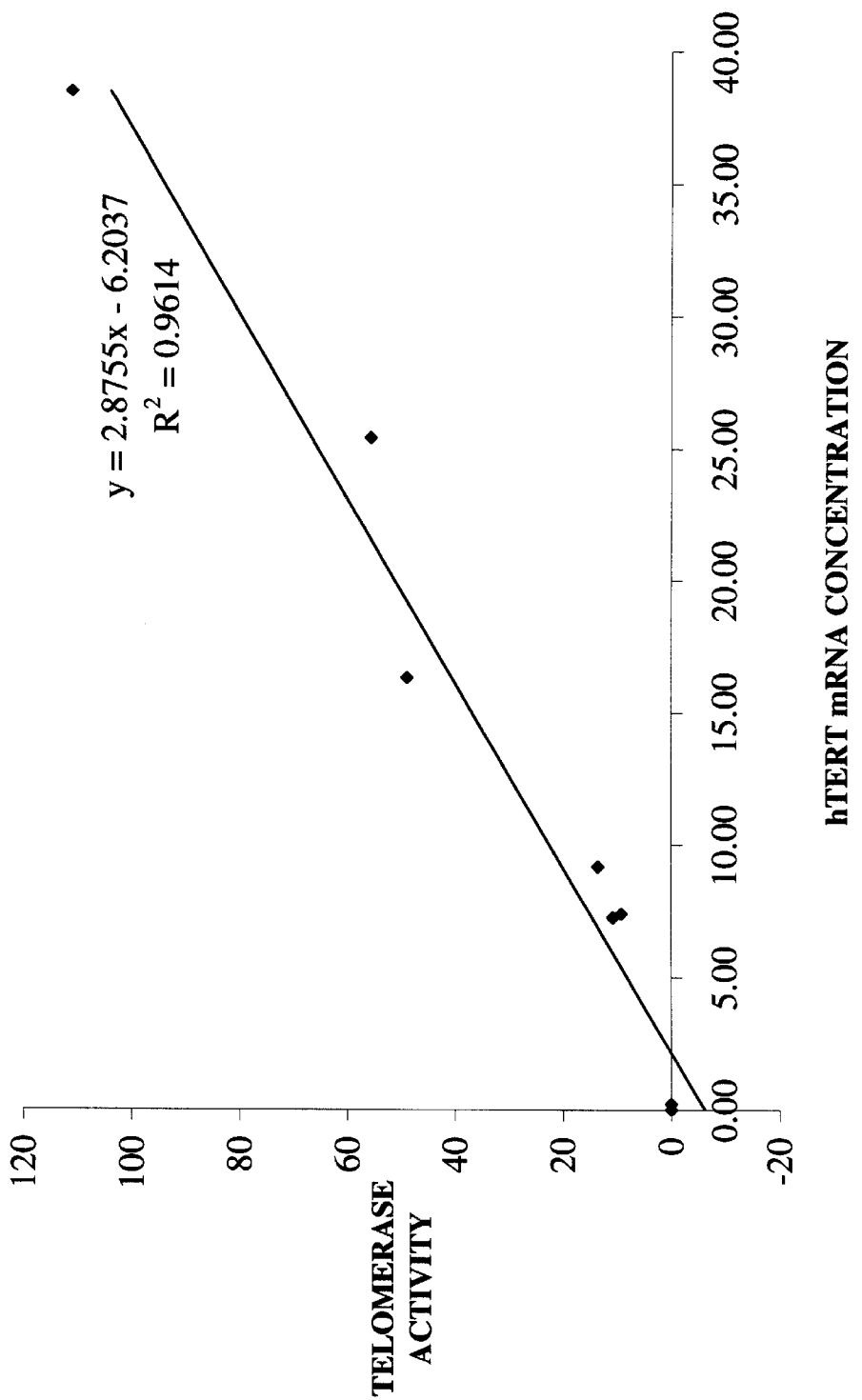
FIG. 3 shows a scatter plot of the telomerase activity relative to hTERT mRNA expression, as described in Example 5.

A scatter plot of the telomerase activity and adjusted hTERT mRNA concentration for each sample is shown in FIG. 3. As is apparent from a visual inspection of FIG. 3, the data strongly suggest that the telomerase activity is linearly related to the hTERT mRNA concentration.

A best-fit linear predictor of telomerase activity from the adjusted hTERT mRNA concentration was calculated by the least squares method. The linear predictor was described by the following equation:

telomerase activity=$C_1$*[hTERT]+$C_2$, where $C_1$=2.8755 and $C_2$=−6.2037.

The $C_2$ value represents the telomerase activity corresponding to no hTERT mRNA concentration and, thus, would be expected to be zero. The negative $C_2$ obtained likely is an statistical artifact. However, a negative $C_2$ also would result if the dependence of the measured telomerase activity upon hTERT mRNA concentration is not linear at low concentrations, but exhibits a threshold phenomenom. The positive "x-intercept" (2.1574) of the prediction line can be interpreted as the threshold mRNA concentration below which telomerase activity is undetectable using this particular activity assay.

The square of the Pearson product moment correlation coefficient was calculated to be $r^2$=0.9614. The $r^2$ value can be interpreted as the fraction of the variance in telomerase activity that can be explained by the hTERT mRNA concentration. The $r^2$ of over 96% indicates that using the hTERT mRNA as a predictor of telomerase acitivity provides an accurate measure of telomerase activity.

It will be clear the particular telomerase activity assay used is not a critical part of the invention. For example, as similar telomerase activity assay is described in Gelmini et al., 1998, Clinical Chemistry 44(10):2133–2138, incorporated herein by reference. To use an alternative telomerase activity assay, analogous experiments are carried out in order to calculate a best-fit linear predictor of telomerase activty from hTERT mRNA concentration. Telomerase activity, expressed in units defined by the assay used, then is estimated from the hTERT mRNA concentration using the calculated predictor analogously.

EXAMPLE 6

Quantitation of hTERT mRNA: Kinetic PCR Format

This example describes the quantitation of hTERT mRNA using a probe-less "kinetic PCR" format, essentially as described in Higuchi and Watson, 1999, in PCR Applications, supra, Chapter 16.

Amplifications are carried out preferably using either ethidium bromide or SYBR® Green I (Molecular Probes, Eugene, Oreg.) in the reaction. Both dyes increase their fluorescence upon intercalation into the double-stranded DNA. Because amplification results in the synthesis of double stranded products, the increase in product amount results in an increase in reaction fluorescence.

Amplifications using ethidium bromide are carried out essentially using the reactions conditions described above for the TaqMan assay, but with 1 μg/ml of ethidium bromide added to the reaction and without the probe). Amplifications using SYBR® Green I are carried out essentially the same, but with 0.2 X SYBR® Green I (sold as 10,000 X) diluted in DMSO.

Reactions using SYBR® Green I are carried out using a GeneAmp® 5700 Sequence Detection System (PE Biosystems, Foster City, Calif.) using the same thermal cycling conditions described above for the TaqMan assay. The GeneAmp® 5700 Sequence Detection System is designed for use with SYBR® Green I and the excitation and detection wavelengths are pre-set for this dye. Reactions using ethidium bromide are carried out using a ABI PRISM® 7700 Sequence Detection System (PE Biosystems, Foster City, Calif.), which allows the selection of suitable detection wavelengths.

The accumulation of amplified product is monitored during the reaction by measuring the dye fluorescence at each cycle, as in the TaqMan reactions described above. Analysis of the fluorescence data to provide a quantitative estimate of sample copy number is carried out essentially as described for the TaqMan assay, above.

EXAMPLE 7 hTERT mRNA Expression in Prostate Cancer Clinical Tissues

Quantitation of hTERT mRNA expression was carried out using prostate biopsies from nine different individuals, designated R1 to R9. The tissue states were classified by pathologists.

Single tissue samples were taken from individuals R1–R4. The tissue samples from individuals R1 and R2 were classified as normal tissue. The tissue samples from individuals R3 and R4 were classified as tumor samples. Paired tumor and 'normal' biopsies were taken from individuals R5–R9. The 'normal' sample was resected from a region of the prostate adjacent to the tumor. Samples of 200 ng total RNA were prepared from the prostate biopsies essentially as described in example 1, In addition, a 200 ng sample of commercially available human prostate total RNA (Clonetech, Palo Alto, Calif.) was analyzed as a negative control (designated "NC", below). The commercially available prostate total RNA was identified as from normal tissue by the supplier.

Quantitation was carried out using a TaqMan assay as described above. As described in the previous examples, amplifications of 10-fold serially diluted hTERT positive control samples were carried out to generate a standard curve. The estimates of initial hTERT mRNA concentration were adjusted based on the separately measured EF1A mRNA concentration, as described above.

Figure 4:
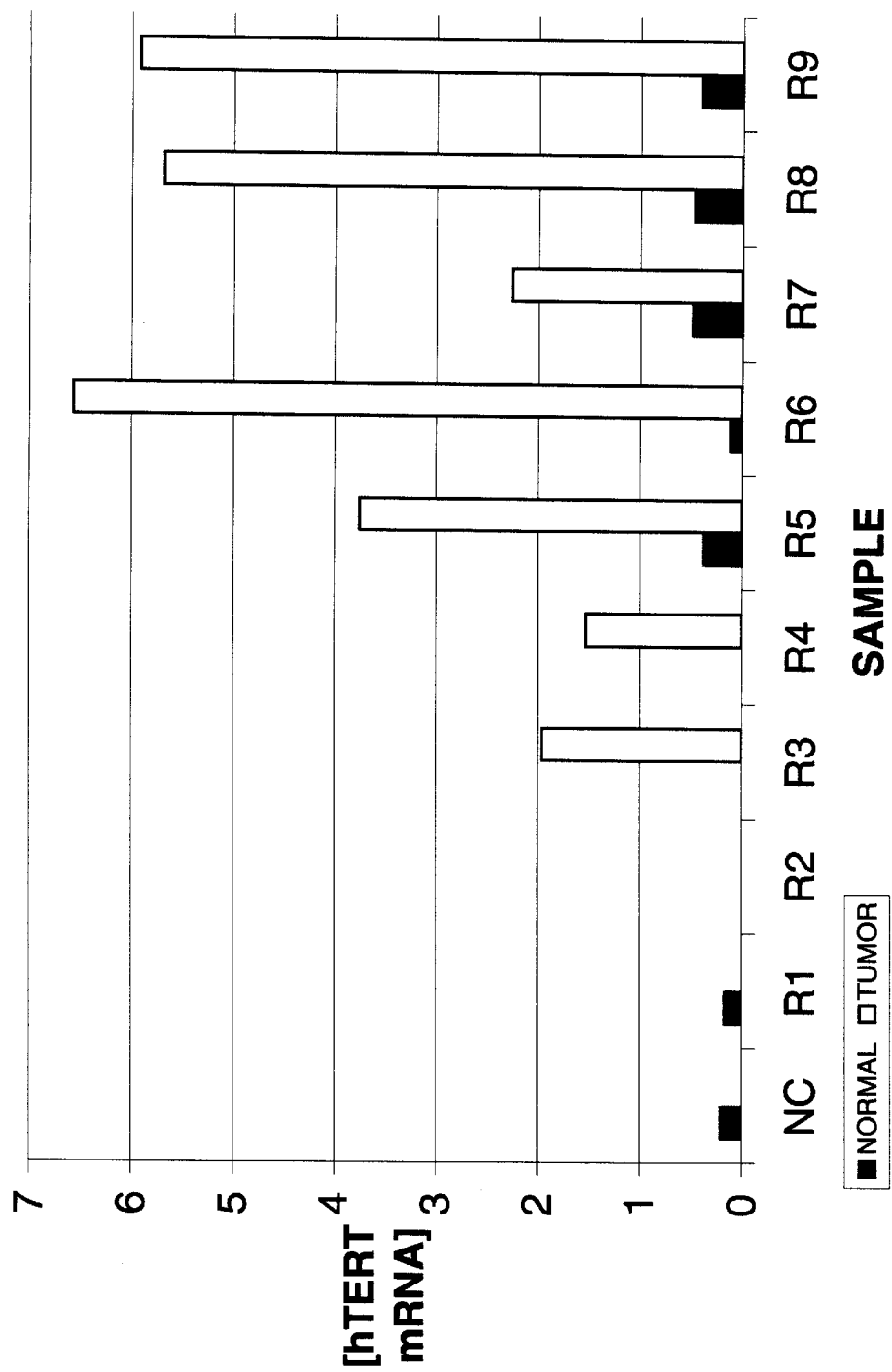
FIG. 4 shows the comparison of hTERT mRNA expression in normal and cancerous prostate tissues, as described in Example 7.

The results are provided in the table, below, and in FIG. 4. In order to facilitate comparison in FIG. 4 of the hTERT mRNA concentrations obtained from the normal tissue and tumor tissue samples from the same individual (i.e., from individuals R5–R9), the two values are shown side-by-side.

| Sample | hTERT mRNA Concentration (copies/ng) | |
|---|---|---|
| | normal cells | tumor cells |
| NC | 0.21 | — |
| R1 | 0.17 | — |
| R2 | 0.00 | — |
| R3 | — | 1.96 |
| R4 | — | 1.53 |
| R5 | 0.37 | 3.75 |
| R6 | 0.12 | 6.57 |
| R7 | 0.49 | 2.26 |
| R8 | 0.47 | 5.68 |
| R9 | 0.40 | 5.92 |

The negative control sample (commercially available normal prostate tissue) exhibited a low, basal level of hTERT mRNA expression. Similarly, the normal prostate tissues exhibited either a low, basal level of hTERT mRNA expression or, with R2, no hTERT mRNA expression.

In contrast, all samples of cancerous prostate tissue exhibited a significantly elevated level of hTERT mRNA expression. The range of hTERT mRNA expression observed in the cancerous tissues samples did not overlap with the range of hTERT mRNA expression observed in normal samples. This demonstrates that the level hTERT mRNA expression can be used to discriminate cancerous from normal tissues.

To discriminate cancerous from normal tissues, a threshold value is selected that is greater than the maximum hTERT mRNA expression observed in normal sample and less than the minimum hTERT mRNA expression observed in cancerous tissues. Tissues with an hTERT mRNA expression greater than the threshold are identified as cancerous. It is expected that some cancerous tissues will be encountered, particularly those in the early stages of becoming cancerous, in which the hTERT mRNA expression may not exceed that threshold of normal expression levels. To maximize the sensitivity of the test, the threshold value should be selected to be as low as possible while still encompassing the range of hTERT mRNA expression in normal tissue.

We claim:

1. A method for identifying the presence of cancerous cells in a human sample wherein said method comprises:
   (a) determining the quantity of hTERT mRNA comprising β-region coding sequence in said sample and in a control sample of non cancerous cells by:
      (1) contacting RNA from said sample and said control sample with a pair of primers, wherein said pair of primers consists of a first primer which hybridizes within exon 8 of the hTERT gene and a second primer which hybridizes upstream of exon 7 or downstream of exon 8 of the hTERT gene;
      (3) measuring the generation of amplification products;
      (4) determining the quantity of hTERT mRNA comprising β-region coding sequence in said sample from the results obtained in step (3); and
   (b) identifying the presence of cancerous cells in said sample if the quantity of hTERT mRNA comprising β-region coding sequence in said sample is greater than the quantity of hTERT mRNA comprising β-region coding sequence in said control sample.

2. The method of claim 1, wherein said second primer hybridizes upstream of exon 7 of the hTERT gene.

3. The method of claim 2, wherein said second primer hybridizes within exon 6 of the hTERT gene.

4. The method of claim 1, wherein said second primer is SYC1118 (SEQ ID NO:5), SYC1076 (SEQ ID NO:2) or SYC1078 (SEQ ID NO:3).

5. The method of claim 1, wherein said first primer is SYC1097 (SEQ ID NO:4).

6. The method of claim 1, wherein the second primer hybridizes within exon 9.

7. The method of claim 1, wherein the amplification reaction is a polymerase chain reaction.

8. The method of claim 1, wherein step (3) is carried out using a probe that is complementary or substantially complementary to said amplification products.

9. The method of claim 8, wherein said probe is selected from the group consisting of CS12 (SEQ ID NO:6), CS1 (SEQ ID NO:7) and CS3 (SEQ ID NO:8).

10. The method of claim 1, wherein step (2) additionally comprises amplifying the nucleic acid sequence in the presence of a probe which hybridizes to the nucleic acid sequence.

11. The method of claim 10, wherein the probe is labeled.

* * * * *